United States Patent
Danger et al.

(10) Patent No.: US 6,368,107 B2
(45) Date of Patent: *Apr. 9, 2002

(54) DENTAL TOOL

(75) Inventors: Karl-Heinz Danger, Detmold; Michael Küllmer, Lemgo, both of (DE)

(73) Assignee: Gebr. Brasseler GmbH & Co. KG, Lemgo (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/514,398

(22) Filed: Feb. 28, 2000

(51) Int. Cl.$^7$ ................................. A61C 3/06
(52) U.S. Cl. ...................................... 433/166
(58) Field of Search ................ 433/165, 166, 433/125

(56) References Cited

U.S. PATENT DOCUMENTS

| | | | | |
|---|---|---|---|---|
| 1,813,741 A | * | 7/1931 | Harper | 433/165 |
| 3,971,135 A | * | 7/1976 | Leu | 433/165 |
| 4,834,655 A | * | 5/1989 | Kyotani | 433/166 |
| 4,990,088 A | * | 2/1991 | Weissman | 433/165 |
| 5,429,504 A | * | 7/1995 | Peltier et al. | 433/165 |

FOREIGN PATENT DOCUMENTS

DE 0 071 611 B1 11/1984

OTHER PUBLICATIONS

EPO Communications dated Apr. 6, 2001 with attached Observations dated Feb. 18, 2001 from Busch & Co. KG (with translation of Feb. 18, 2001 cover letter and translation of two pages of Observations).

Busch & Co. KG catalog "Diamond Instruments," 1992/93, catalog cover pages and page 4.

Hager & Meisinger GmbH catalog "Dental 97," "CE Diamond Instruments," 1997, catalog cover pages and p. 57.

NTI–Kahla GmbH, catalog "FG–Turbo Diamond Instruments," Sep. 1998, catalog cover pages and pp. 1 and 2.

Busch & Co. KG catalog "Longlife Perio–Pro," Mar. 1997 (with translation).

Gebr. Brassler GmbH catalog "Rotary Instruments for Dental Practice and the Practice Laboratory," 1989, catalog cover pages and p. 3.11 (with translation).

Gebr. Brassler GmbH catalog "Surface Design of Restoration Materials, " 1995, catalog cover pages and pp. 10 and 11 (with translation).

European Standard EN–ISO 7711–3, Standards Committee Dental in the DIN Deutsches Institut Für Normung e.V. (German Standards Institute), Nov. 1995. pp. 1–3 (with translation).

* cited by examiner

Primary Examiner—Nicholas D. Lucchesi
(74) Attorney, Agent, or Firm—Lyon & Lyon LLP

(57) ABSTRACT

The present invention relates to a dental tool, in particular for grinding teeth, comprising a grinding head and a rotatingly drivable shaft, the grinding head being provided on its surface with at least one elevated portion which, during rotation of the grinding head works a surface to be prepared and defines a circle of rotation. The invention is characterized in that the elevated portion comprises an edge, and the edge is the side line of a surface that is situated at least at the leading side of the edge and that is retracted relative to the circle of rotation defined by the edge.

20 Claims, 3 Drawing Sheets

Fig.7A
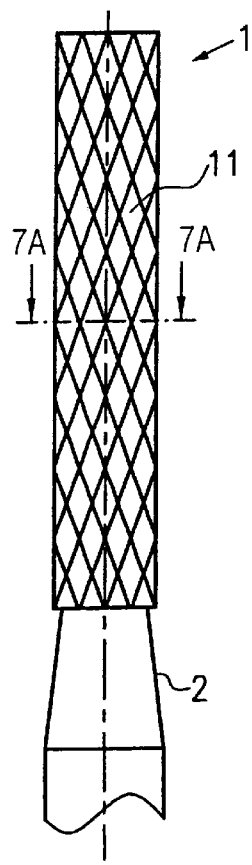
Fig.8A
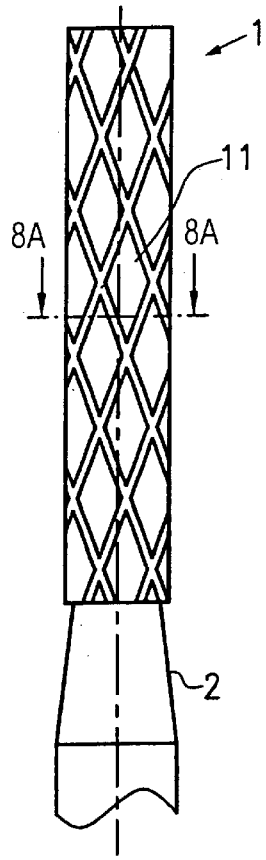
Fig.9A
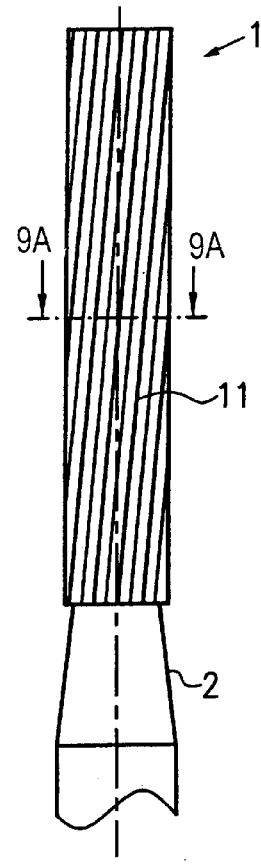
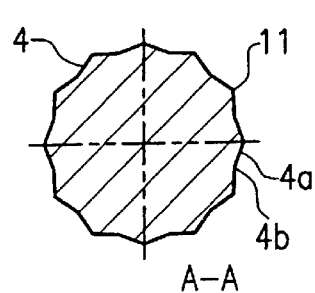
Fig.7B
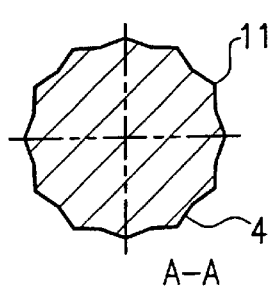
Fig.8B
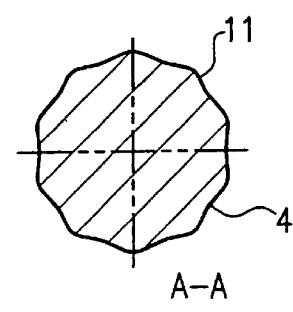
Fig.9B

DENTAL TOOL

RELATED APPLICATIONS

Benefit of priority for this invention is claimed, under 35 U.S.C. § 119 and all other applicable law, to the inventors' earlier German patent application, Number 199 08 507.2, filed in the Deutsches Patentamt on Feb. 26, 1999.

BACKGROUND

The present invention relates to a dental tool, in particular a dental tool for grinding teeth.

Dental tools for grinding teeth, as are known from for example from the generic disclosure of EP 71 611 B1, are used in dental preparatory techniques for both pre-grinding (roughing) and fine grinding (smoothing) operations. In these grinding or abrading processes the dentist and also the patient want the procedure to be completed as fast as possible. Here, however, a conflict of interests arises. The dentist must prepare the tooth in such a way that it can subsequently be restored again. The dentist should not remove too much material. Nor should there be any avoidable damage caused by, for example, high preparation temperatures. In this regard it should be noted that normally the amount of material removed should be as small as possible. A preparation is needed that is gentle on the tooth substance and that preserves it.

This, however, is not possible for all preparatory work. For instance, when a tooth is prepared that is to be provided with a crown or bridge in a later step, a relatively large amount of material must be removed by the dentist depending on the individual case. The instruments used for this are available with different grain sizes. Many dentists prefer coarse grinding instruments to achieve a reduction of the dental enamel as quickly as possible. The known grinding instruments, however, are in need of improvement as to their efficiency, i.e. a fast reduction of the dental enamel is desirable from the viewpoint of the dentist and also from that of the patient.

It is one object of the present invention to provide a dental tool that in practice achieves a higher removal rate with respect to a surface to be treated. Other objects of the invention are described herein.

According to the invention this object is achieved by a dental tool, in particular a tool for grinding teeth, comprising a grinding head and a rotatingly drivable shaft, the grinding head having on its surface at least one elevated portion that, during revolution of the grinding head, works or treats a surface to be prepared and defines a circle of rotation. The dental tool is characterized in that the elevated portion comprises and edge, the edge forms the side line of a surface that is situated at least at the leading side of the edge and that is recessed relative to the rotation circle defined by the edge.

The dental tool of the invention is characterized by several advantages. Due to the arrangement of a grinding head having at least one elevated portion comprising an edge, and in contrast to known grinding instruments that have a conical or cylindrical surface, a higher contact pressure is achieved at the working area or elevated portion at a constant pressure force exerted by a dentist during the grinding or abrading operation, which results in a greater amount of removal. In the known grinding instruments a larger contact surface contacts the tooth per unit time, so that the constant contact force is distributed over a larger surface area.

At the same time, however, the tooth surface may be worked or treated over the entire external length of the grinding head of the invention. As a result, in various embodiments described herein the trailing sections of the edge contact the tooth surface during each revolution of the grinding head at a certain time delay that depends on the rotational speed of the grinding head and the pitch or other configurational arrangement of the elevated portion.

The configuration of a grinding head having an elevated portion comprising an edge has the additional effect that edges represent a known geometrical shape and, in addition, have a great strength, which is of special importance to grinding tools. Moreover, edges can be produced in different ways, depending on the shape of the blank used in manufacturing the tool, so that a simple and inexpensive production method can be chosen.

Because the edge forms the side line of a surface that is situated at least at the leading side of the edge and is recessed relative to the rotation circle defined by the edge, in the course of rotation of the dental tool the elevated edge or side line of the recessed surface comes into contact with the tooth surface to be treated from its initial contact point up to its end or trailing contact point. In this manner, both the interests of the dentist and those of the patient to be treated are satisfied with the dental tool of the invention by way of the trailing removal of dental enamel through the higher contact pressure per working area at a constant contact force exerted by a dentist.

Preferably, the grinding head is substantially conical, so that the known advantages of conical shaped grinding heads are additionally achieved by the conical grinding heads of the invention.

According to another advantageous aspect of the invention, the recessed surface or surfaces may be planar (that is, substantially flat in cross-section) or have a concave curvature. Such shapes of the surfaces can be produced in a particularly easy manner. Moreover, instead of being concavely curved, the recessed surface may also consist of two sections intersecting each other at an obtuse angle, as in an indented wedge shape.

To improve the efficiency of the dental tool of the invention, not only one edge, but several edges of a similar type should be formed on the circumference of the grinding head. It is possible for example to form a plurality of adjacent, recessed planar surfaces on the outer circumference of the grinding head that are separated one from the next by elevated curved portions remaining in the originally conical grinding head following tooling. Alternatively, two planar surfaces may also adjoin each other directly.

When the elevated curved portion is positioned in the outer (rotation) circle of the dental tool of the invention, the configuration allows excellent guidance of the tool on the tooth to be treated without impairing the other inventive effects.

According to an alternative embodiment of the dental tool of the invention, the elevated portion comprises an edge that is threaded over the length of the grinding head. As a result, a multitude of point-like sections of the edge simultaneously engage into the surface of the tooth per time unit and at a corresponding pitch of the thread-like edge. Hence, although the contact pressure as divided among the multitude of engaging pointlike sections, at a constant contact force per working surface area, is smaller than would occur with a single engaging point-like section, it is still greater than the contact pressure of known cylindrical or conical heads. Moreover, the working surface is still at least twice the size of a smooth circumferential surface of the conventional grinding instruments and may also be many times that size provided that the pitch of the thread is appropriately chosen.

To achieve a production of a thread-like edge as simply as possible, the elevated portion may comprise a rounded elevated surface similar to a screw thread.

According to a further alternative embodiment of the dental tool of the invention, the edges are part of a honeycomb-like structure consisting of alternating fields circumferentially offset one from the next along the longitudinal length of the grinding head. Preferably, each of said alternating fields comprises a plurality of elevated portions comprising edges, and a plurality of recessed surfaces adjoining said edges. This is of advantage insofar as, in the case of a substantially circular cross-section of the grinding head of the invention, a multitude of edges can be formed on the surface of the grinding head.

According to another aspect of the invention, the grinding head comprises at least two longitudinally successive sections and the edges of the first section are arranged in a circumferentially-offset fashion relative to the edges of the other section. Such a configuration guarantees that a given edge contacts the tooth only sectionwise, resulting in a high contact pressure. This above embodiment can be implemented in a particularly simple way when the edges extend in the longitudinal direction of the dental tool, because such a configuration yields a particularly simple and easily-producible geometrical shape.

The offset arrangement of the edges can specifically be chosen such that the edges of the next sections but one are substantially identical in orientiation. Other alternations of offset among the multiple sections will be recognized by those skilled in the art in view of the present disclosure. A particularly advantageous relation between treatment time and removal rate can thereby be achieved.

According to another development of the invention, when several edges are provided that intersect one another forming a rhombic pattern, it is possible to remove a great amount of material without the above-explained drawbacks of the prior art being observed.

A configuration that can be produced in a particularly simple way is obtained when a concave curvature is provided at both sides of a rounded edge, resulting in an approximately waved design. Such a design can not only be produced easily, but due to the absence of corners is also devoid of any stress peaks, and yields a dental tool has a particularly long service life.

In addition, and in contrast to conventional conical grinding instruments, the surface area of the grinding head is macroscopically enlarged, whereby an increased number of grinding grains can be placed on the grinding head.

In all of the above-mentioned preferred embodiments of the dental tool according to the invention, the surface of the grinding head preferably has diamond grinding grains placed thereon for increasing the removal rate. The diamond grains may either have the same grain size or different grain sizes. The grain sizes of the diamond grains range from about 5 to 250 µm, preferably 100 to 180 µm. The selection of the grain size will, in turn, have an effect on the removal efficiency with respect to the dental enamel and should thus be adapted to the requirements of the dental tool.

Further advantages and features of the present invention will become apparent from the following detailed description of inventive embodiments of a dental tool in conjunction with the attached drawings.

DESCRIPTION OF THE DRAWINGS

FIG. 7A is a schematic side view of a seventh embodiment of a dental tool according to the invention.

FIG. 7B is a cross-sectional view taken along line 7A—7A of FIG. 7A.

FIG. 8A is a schematic side view of an eighth embodiment of a dental tool according to the invention.

FIG. 8B is a cross-sectional view taken along line 8A—8A of FIG. 8A.

FIG. 9A is a schematic side view of a ninth embodiment of a dental tool according to the invention.

FIG. 9B is a cross-sectional view taken along line 9A—9A of FIG. 9A.

DETAILED DESCRIPTION

Figure 1A:
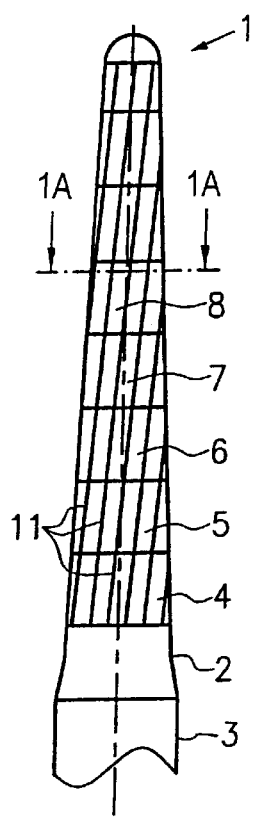
FIG. 1A is a schematic side view of a first embodiment of a dental tool according to the invention.
Figure 2A:
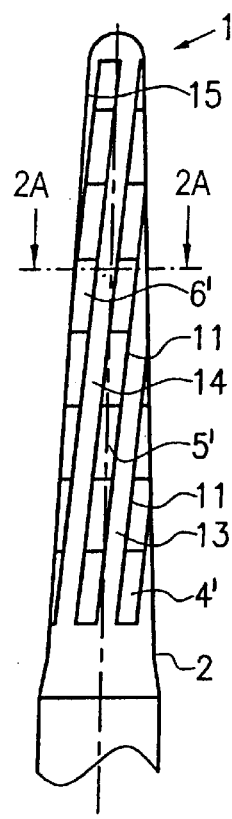
FIG. 2A is a schematic side view of a second embodiment of a dental tool according to the invention.
Figure 3A:
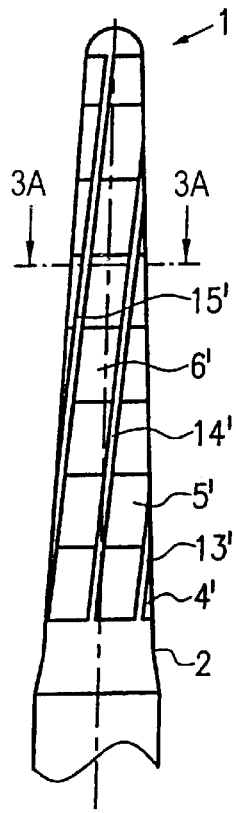
FIG. 3A is a schematic side view of a third embodiment of a dental tool according to the invention.

FIG. 1A is a schematic side view showing a first embodiment of a dental tool 1 according to the invention. The dental tool 1 is used for grinding or abrading teeth and comprises a grinding head 2 and a rotatingly drivable shaft 3 The shaft 3 is here driven by a driving means (not shown).

Figure 1B:
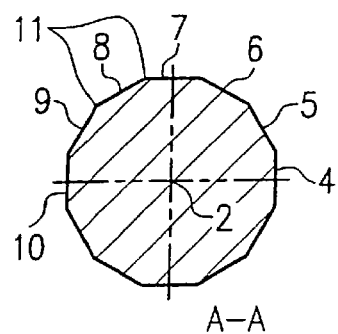
FIG. 1B is a cross-sectional view taken along line 1A—1A of FIG. 1A.
Figure 2B:
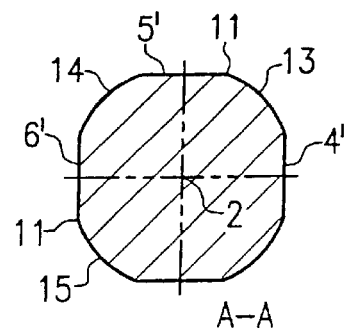
FIG. 2B is a cross-sectional view taken along line 2A—2A of FIG. 2A.
Figure 3B:
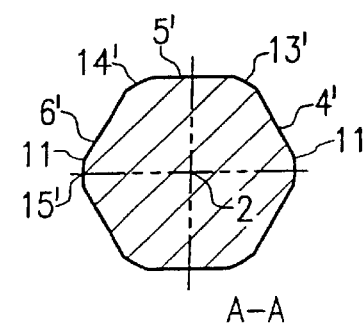
FIG. 3B is a cross-sectional view taken along line 3A—3A of FIG. 3A.

In the embodiment shown in FIGS. 1A and 1B, the grinding head 2 is substantially conical. The grinding head 2 as well may be cylindrical or flame shaped. Furthermore, planar recessed surfaces 4 to 10 are incorporated into the circumferential surface of the grinding head 2. Each two such respective planar surfaces are adjacent to each other, such that elevated portions 11, which in the present embodiment comprise edges 11 seen in the sectional view of FIG. 1B, are formed along the connection line between the respective planar surfaces 4 to 10. In other words, the edges 11 form the side lines of the planar surfaces 4 to 10. In FIGS. 1A and 1B, only three edges and two edges, respectively, have been designated with the corresponding reference numeral 11 by way of example, although six such edges are visible in FIG. 1A and twelve such edges in FIG. 1B. Similarly, FIGS. 1A and 1B show additional planar surfaces beyond those designated with reference numerals 4 though 10; and these and other figures herein depict multiple structural features that are described but not individually enumerated in the drawings.

As seen in FIG. 1B, the circumferential surface of the grinding head 2 is subdivided into twelve recessed planar surfaces sections. The side view of FIG. 1A shows a number of these recessed surfaces spiraling longitudinally along the length of the grinding head. This particular subdivision, however, is not imperative. Another number can also be chosen for the subdivision. The number, and also the orientation of the subdivided sections, depends on the respective requirements.

The different sections of the grinding head, as for example the subdivided sections exemplified above, may each be electroplated with different abrasives, such as diamond grains. At the same time, the different sections may also comprise diamond grains of different grain sizes ranging from 5 to 250 μm. Of course, the different sections may also be covered with diamond grains having the same grain size. A size of the diamond grains that ranges from 100 to 180 μm has turned out to be particularly efficient with respect to the grinding effect.

Finally, it should be noted that in the inventive dental tool shown in FIG. 1A the tip of the grinding head 2 is rounded to prevent injuries when the inventive dental tool is used in a patient's mouth.

The operation of the dental tool 1 according to the invention is described in the following example.

The dental tool 1 is inserted with its shaft 3 into a driving means (not shown) which upon use of the dental tool 1 according to the invention will rotatingly drive the shaft 3 including the grinding head 2. Subsequently, the dental tool 1 of the invention is moved towards a tooth together with its grinding head 2. It is only the edges 11 that will come into contact with the surface of the tooth. Since the twist or helix angle of the edges 11 in FIG. 1A is about 30°, the grinding head 2 must rotate by 30° to ensure that an edge 11 contacts a tooth surface from its initial point to its end point (for example, from the tip-most point of the edge to the end point on the edge closest the base of the grinding head).

Hence, at a given moment an edge 11 comes into contact with a tooth surface only pointwise and not over its entire length, resulting in an increased contact pressure at the working surface at a constant contact force. Nevertheless, a tooth surface is treated by an edge 11 over the entire length of the grinding head 2, and succeeding or trailing points along edge 11 will contact the tooth surface at a time delay depending on the rotational speed of the dental tool 1, resulting in a "trailing removal" of tooth material as that term is used herein.

FIGS. 2A, 2B, 3A and 3B show two further embodiments similar to the first embodiment of the dental tool 1 according to the invention. These two embodiments differ from the first embodiment by the feature that a respective one of the elevated curved portions 13, 14, 15 and 13', 14', 15', respectively, derived from the conical shape is situated between each two neighboring recessed planar surfaces, e.g. 4', 5', 6'.

These two embodiments also comprise edges 11 which, however, are provided in a reduced number (FIG. 2B) or in an increased number (FIG. 3B) in dependence upon the arcuate length of the curved portions 13, 14, 15 and 13', 14', 15', respectively.

Figure 4A:
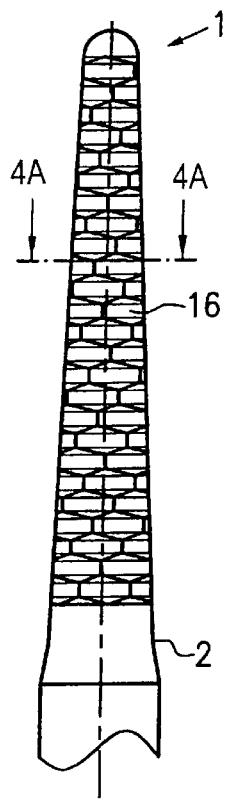
FIG. 4A is a schematic side view of a fourth embodiment of a dental tool according to the invention.

FIG. 4A is a schematic side view showing a fourth embodiment of the dental tool 1 according to the invention. Said embodiment differs from the preceding embodiments in that the grinding head 2 is provided on its surface with a honeycomb-like structure 16. As is particularly shown in FIG. 4B, the honeycomb-like outer structure 16 is formed with elevated portions 18 and recessed or indented portions 17. This becomes apparent from FIG. 4B and the enlarged section marked by the small circle.

Figure 4B:
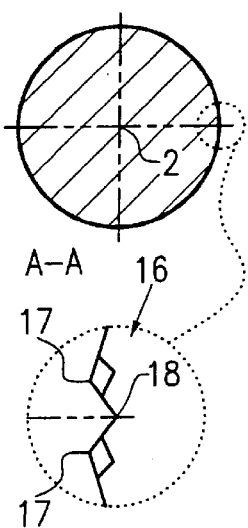
FIG. 4B is a cross-sectional view taken along line 4A—4A of FIG. 4A next to an enlarged illustration of the section marked by the small circle in FIG. 4B.

The sequence of elevated portions 18 and indented portions 17 as illustrated by way of example in FIG. 4B may also be opposite, i.e. the elevated portions may be indented portions and the indented portions may represent elevated portions. This, however, is of no importance to the illustration of a basic principle of the present invention, namely to achieve what is termed a "trailing removal" per revolution of the grinding head 2.

Figure 5A:
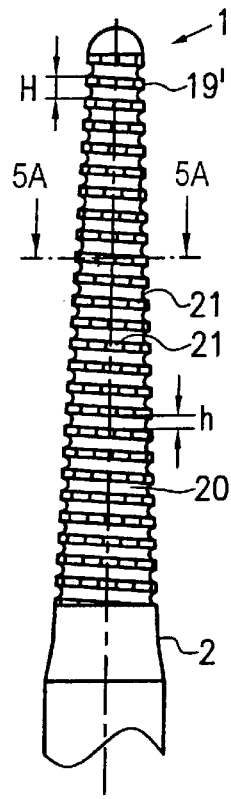
FIG. 5A is a schematic side view of a fifth embodiment of a dental tool according to the invention.
Figure 5B:
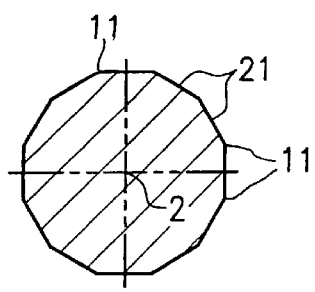
FIG. 5B is a cross-sectional view taken along line 5A—5A of FIG. 5A.

FIG. 5 shows a fifth embodiment of the dental tool according to the invention. In the lateral view of the inventive dental tool 1 of FIG. 5A, the elevated portion 19' is formed over the length of the grinding tool 2 in a spiral or thread-like configuration. The pitch of one thread revolution corresponds to the height h of the spiral groove 20. Upon rotation of the dental tool 1 of the invention, point-like sections of the elevated portion 19' will act on a tooth surface at a given moment. Said point-like sections will move downwards in FIG. 5A upon continued rotation, so that per revolution of the grinding head the height H per winding of the elevated portion 19' will remove dental enamel to be treated in trailing fashion. As shown in FIG. 5B, the surface of the elevated portion may be provided with a multitude of adjacent planar surfaces 21, resulting in a dodecagonal surface in the section shown in FIG. 5B. The corner edges 11 formed between respective adjacent planar surfaces 21 of the elevated portion 19' further enhance the efficiency of the dental tool of the invention.

As can be seen, the number of edge corners 11 of the section shown in FIG. 5B is variable in response to the respective requirements, i.e. the number of corners can be increased or reduced.

Figure 6A:
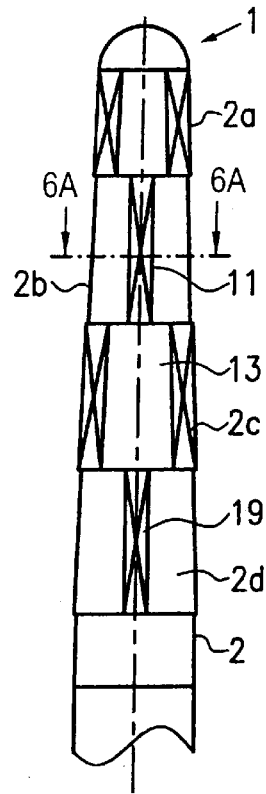
FIG. 6A is a schematic side view of a sixth embodiment of a dental tool according to the invention.
Figure 6B:
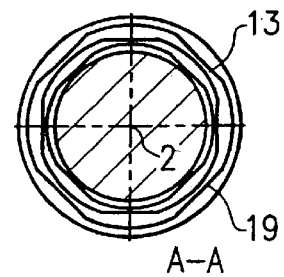
FIG. 6B is a cross-sectional view taken along line 6A—6A of FIG. 6A.

FIGS. 6A and 6B show a sixth embodiment of the dental tool 1 according to the invention. Said dental tool 1 substantially differs from several of the dental tools 1 shown in the preceding embodiments in that the edges 11 forming the elevated portions are not arranged in continuous fashion over the entire length of the grinding head 2. Rather, the grinding head 2 consists of several sections 2a–2d arranged one after the other in the longitudinal direction of the grinding head 2. Four sections 2a–2d are shown in the embodiment, but their number may also be greater or smaller.

As is apparent particularly in FIG. 6A, each of said sections 2a–2d comprises a plurality of edges 11 which in the embodiment extend in parallel with the longitudinal direction of the dental tool 1, but may also be arranged at an angle relative to the longitudinal direction. A planar surface 19 is arranged in front of each edge 11, and a curved portion 13 is provided behind each edge 11, resulting in the cross section shown in FIG. 6B. A further special feature in comparison with the dental tools 1 according to the embodiments shown in FIGS. 1A–5B is that in this configuration the edges 11 of the one section 2a are offset relative to the edges 11 of the subsequent section 2b. The offset arrangement can be chosen such that the edges 11 of all odd sections, i.e. in the present embodiment the first and third section 2a and 2c, and the edges 11 of all even sections, i.e. in the present embodiment the second and fourth section 2b and 2d, are substantially identical.

FIGS. 7A–8B show a seventh and eighth embodiment of the dental tool 1 according to the invention. The two embodiments are similar; they just differ from each other in the number of the edges 11 provided for. In the embodiment shown in FIGS. 7A and 7B the number is greater than in the embodiment shown in FIGS. 8A and 8B. The common feature of the two embodiments is that there are provided at least two edges 11 that extend in opposite directions and in spiral configuration around the grinding head 2, thereby intersecting each other so that the rhombic pattern shown in FIGS. 7A and 8A is obtained. Moreover, in said dental tools 1 the recessed surfaces 4 which are leading with respect to a respective adjoining edge 11 are composed of two sections 4a, 4b that intersect each other at an obtuse angle. As a result, pockets are formed between two respective edges 11; these do not rest on the tooth to be treated, thereby providing a small contact surface of the dental tool 1 as is desired according to the invention.

A ninth embodiment is illustrated in FIGS. 9A and 9B. The edges 11 that form the elevated portions are here rounded. Furthermore, the recessed surfaces 4 that are leading with respect to an adjoining rounded edge 11 are provided with a concave curvature, resulting in a symmetrical waved extension of protruding edges 11 and concave curvatures when viewed in cross section. In the instant embodiment it does not matter whether, as illustrated, the edges 11 extend at an angle relative to the longitudinal axis of the dental tool 1 or whether they are arranged in parallel therewith.

Although this is not drawn in the above figures of various embodiments of the dental tool of the invention, the grinding heads 2 of the various embodiments may be electroplated with diamond grains for an improved grinding effect. The diamond grains may here have identical or also different grain sizes. The preferred size ranges from 100 to 180 $\mu$m at a possible grain size spectrum between 5 and 250 $\mu$m.

It should be noted that in particular in the embodiments 4 and 5, and in contrast to conventional conical grinding instruments, the outer surface area is enlarged so that in comparison with the conventional conical grinding instruments a larger number of diamond grains can be applied. Such a measure results in a further improvement in the efficiency or removal rate of the dental tool 1 of the invention. As a consequence, the prepreration time is further reduced. The result is a more gentle treatment of the patient by the dentist.

It should also be noted that the geometrical and construtional features illustrated in FIGS. 1A to 9B are a part of the description of the present invention, but that they, and the other examples and descriptions herein, do not limit the invention claimed in this patent. The subject matter of this invention is set forth in the claims below, and that invention includes all lawful equivalents of the matter recited in the claims.

What is claimed is:

1. A dental tool for grinding a tooth, comprising
   a rotatingly drivable shaft;
   a grinding head having a first end attached to the rotatingly drivable shaft, the grinding head comprising at least one elevated portion extending from the first end to a second end of the grinding head, the elevated portion oriented at a helical angle about the periphery of the grinding head, and the elevated portion comprising an edge for grinding the tooth;
   wherein a single point on the edge contacts the tooth at any given moment during grinding, succeeding points along the edge contacting the tooth as the grinding head is rotated, thereby utilizing an entire length of the edge for grinding the tooth.

2. A dental tool according to claim 1 comprising a plurality of said elevated portions forming a plurality of edges for grinding the tooth.

3. A dental tool according to claim 1 wherein the grinding head further comprises a planar recessed surface on a leading side of the at least one elevated portion.

4. A dental tool according to claim 1 wherein the second end comprises a rounded tip.

5. A dental tool according to claim 1 wherein the grinding head is one of a conical, cylindrical, and flame shape.

6. A dental tool according to claim 1 wherein the edge is rounded.

7. A dental tool according to claim 6 wherein the grinding head further comprises a recessed surface on a leading side of the elevated portion, the recessed surface having a concave curvature.

8. A dental tool according to claim 1 wherein the grinding head further comprises a diamond grain surface for grinding the tooth.

9. A dental tool for grinding a tooth, comprising
   a rotatingly drivable shaft;
   a grinding head attached to the rotatingly drivable shaft, the grinding head comprising a honeycomb-like surface including elevated and recessed portions, each elevated portion comprising an edge for grinding the tooth, the honeycomb-like surface comprising a plurality of alternating fields circumferentially offset from one another along a longitudinal length of the grinding head to facilitate grinding the tooth over the entire length of the grinding head when the grinding head is rotated.

10. A dental tool for grinding a tooth, comprising
    a rotatingly drivable shaft;
    a grinding head having a first end attached to the rotatingly drivable shaft, the grinding head comprising an elevated portion threaded around the periphery of the grinding head, the elevated portion extending from the first end to a second end of the grinding head and comprising an edge for grinding the tooth;
    wherein multiple points on the edge contact the tooth at any given moment, succeeding points along the edge contacting the tooth as the grinding head is rotated thereby utilizing an entire length of the edge for grinding the tooth when the grinding head is rotated.

11. A dental tool according to claim 10 wherein the grinding head further comprises a planar recessed surface on a leading side of the elevated portion.

12. A dental tool according to claim 10 wherein the edge is rounded.

13. A dental tool according to claim 10 wherein the grinding head further comprises a diamond grain surface for grinding the tooth.

14. A dental tool for grinding a tooth, comprising
    a rotatingly drivable shaft;
    a grinding head attached to the rotatingly drivable shaft, the grinding head comprising a plurality of sections situated one after the next along a longitudinal length of the grinding head, the plurality of sections each comprising a plurality of elevated edges;
    wherein the plurality of elevated edges of one section are circumferentially offset relative to the plurality of elevated edges of a next section, the plurality of elevated edges grinding the tooth when the grinding head is rotated.

15. A dental tool according to claim 14 wherein the grinding head further comprises a planar recessed surface on a leading side of the plurality of elevated edges and a curved recessed surface on a trailing side of the plurality of elevated edges, the planar recessed surface meeting the curved recessed surface.

16. A dental tool according to claim 14 wherein the plurality of elevated edges of every other section along the longitudinal length of the grinding head are substantially identical in circumferential orientation.

17. A dental tool according to claim 14 wherein the grinding head further comprises a diamond grain surface for grinding the tooth.

18. A dental tool for grinding a tooth, comprising
a rotatingly drivable shaft;
a grinding head having a first end attached to the rotatingly drivable shaft, the grinding head comprising a plurality of elevated portions extending from the first end to a second end of the grinding head, the elevated portions intersecting one another to form a rhombic pattern, the plurality of elevated portions each comprising an edge for grinding the tooth;
wherein the edges grind the tooth when the grinding head is rotated.

19. A dental tool according to claim 18 wherein the grinding head further comprises a recessed surface on a leading side of each elevated portion, the recessed surface comprising two sections intersecting each other at an obtuse angle to form a pocket.

20. A dental tool according to claim 18 wherein the grinding head further comprises a diamond grain surface for grinding the tooth.

* * * * *